(12) United States Patent  (10) Patent No.: US 9,966,537 B2
Gray et al.  (45) Date of Patent: May 8, 2018

(54) COMPOSITIONS WITH 2,3-DISUBSTITUTED INDOLES AS CHARGE TRANSPORT MATERIALS, AND DISPLAY DEVICES FABRICATED THEREFROM

(71) Applicant: Dow Global Technologies LLC, Midland, MI (US)

(72) Inventors: Kaitlyn Gray, Freeland, MI (US); Robert Wright, Sugarland, TX (US); Liam Spencer, Manvel, TX (US); David Devore, Midland, MI (US); David Pearson, Lake Jackson, TX (US); Jichang Feng, Shanghai (CN); Jing Jing Yan, Shanghai (CN); Shaoguang Feng, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days. days.

(21) Appl. No.: 15/539,856

(22) PCT Filed: Dec. 22, 2015

(86) PCT No.: PCT/CN2015/098252
§ 371 (c)(1),
(2) Date: Jun. 26, 2017

(87) PCT Pub. No.: WO2016/107459
PCT Pub. Date: Jul. 7, 2016

(65) Prior Publication Data
US 2017/0373253 A1    Dec. 28, 2017

Related U.S. Application Data

(60) Provisional application No. 62/097,213, filed on Dec. 29, 2014.

(51) Int. Cl.
C07D 209/86    (2006.01)
H01L 51/54    (2006.01)
(Continued)

(52) U.S. Cl.
CPC ........ *H01L 51/0061* (2013.01); *C07D 209/86* (2013.01); *H01L 51/0072* (2013.01);
(Continued)

(58) Field of Classification Search
CPC .................................................. C07D 209/86
See application file for complete search history.

(56) References Cited

U.S. PATENT DOCUMENTS
6,706,423 B2    3/2004    Lin et al.
6,790,539 B2    9/2004    Lin
(Continued)

FOREIGN PATENT DOCUMENTS
JP    3229654 B2    11/2001
JP    3945123 B2    7/2007
(Continued)

*Primary Examiner* — Daniel Shook
(74) *Attorney, Agent, or Firm* — Husch Blackwell LLP

(57) ABSTRACT

Provided is a composition comprising a compound selected from Structure 1, as described herein:

(Structure 1)

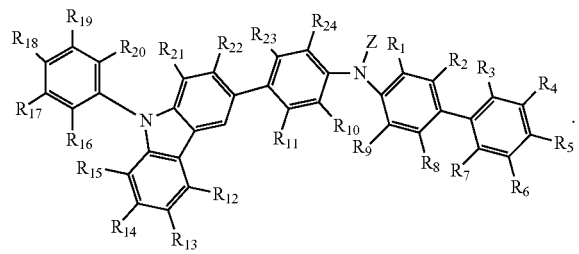

15 Claims, 1 Drawing Sheet

(51) Int. Cl.
*H01L 51/00* (2006.01)
*H01L 51/50* (2006.01)

(52) U.S. Cl.
CPC ...... *H01L 51/5012* (2013.01); *H01L 51/5056* (2013.01); *H01L 51/5072* (2013.01); *H01L 51/5088* (2013.01); *H01L 51/5092* (2013.01)

(56) References Cited

U.S. PATENT DOCUMENTS

| | | | |
|---|---|---|---|
| 7,846,559 B2 | 12/2010 | Hwang et al. | |
| 8,247,090 B2 | 8/2012 | Hwang et al. | |
| 8,395,143 B2* | 3/2013 | Lee | C07D 409/10 257/40 |
| 2004/0265629 A1 | 12/2004 | Wang et al. | |
| 2007/0072002 A1 | 3/2007 | Kim et al. | |
| 2010/0018997 A1 | 1/2010 | Faneca | |
| 2010/0244008 A1 | 9/2010 | Lee et al. | |
| 2013/0112948 A1 | 5/2013 | Jung et al. | |
| 2014/0151667 A1 | 6/2014 | Miyata | |
| 2014/0374722 A1 | 12/2014 | Kim et al. | |

FOREIGN PATENT DOCUMENTS

| | | |
|---|---|---|
| JP | 4048525 B2 | 2/2008 |
| JP | 4810805 B2 | 11/2011 |
| JP | 4951829 B2 | 6/2012 |
| WO | 2009061145 A1 | 5/2009 |
| WO | 2010136352 A1 | 12/2010 |
| WO | 2012143079 A1 | 10/2012 |
| WO | 2013109027 A1 | 7/2013 |

* cited by examiner

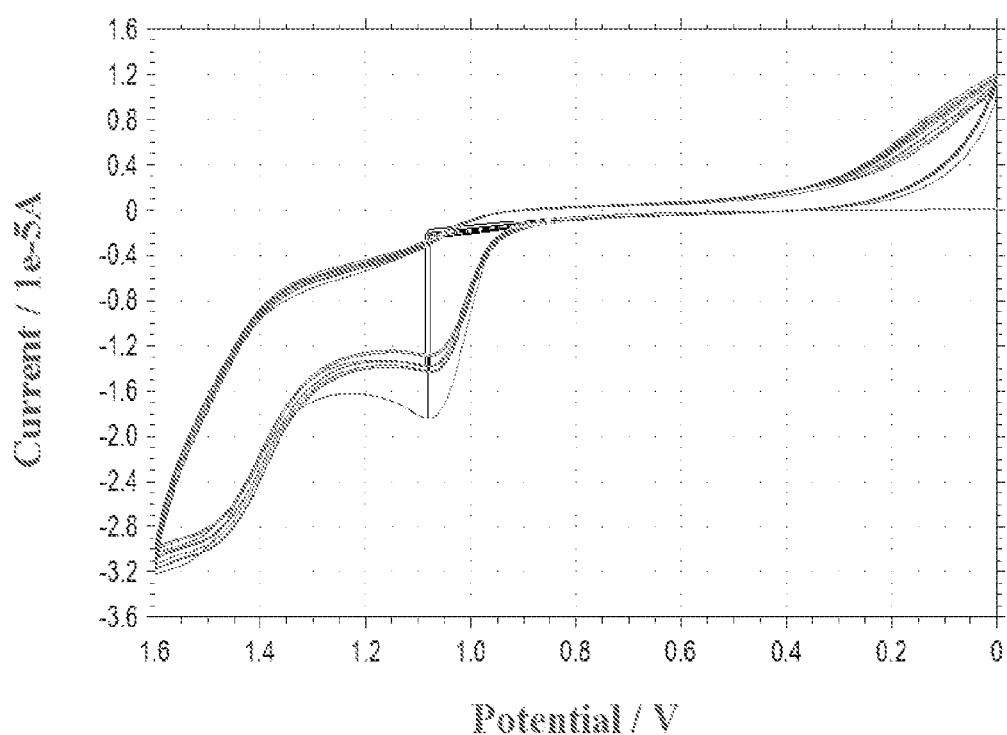

COMPOSITIONS WITH 2,3-DISUBSTITUTED INDOLES AS CHARGE TRANSPORT MATERIALS, AND DISPLAY DEVICES FABRICATED THEREFROM

REFERENCE TO RELATED APPLICATIONS

The present application claims the benefit of U.S. Provisional Application No. 62/097,213, filed Dec. 29, 2014.

BACKGROUND

Organic light emitting devices (OLEDs) are light-emitting diodes (LEDs), which include an emissive electroluminescent layer composed of an organic compound that emits light in response to an electric current. A typical OLED has a multi-layer structure, and typically includes an indium tin oxide (ITO) anode and a metal cathode. Sandwiched between the anode and cathode are several organic layers, such as a hole injection layer (HIL), a hole transport (or transfer) layer (HTL), an emitting material layer (EML), an electron transport (or transfer) layer (ETL), an electron injection layer (EIL), and a hole blocking layer.

In order to improve the performance and lifetime of OLEDs, new electron transport layers (ETLs) and hole transport layers (HTLs) are being targeted. In the case of HTLs, the state of the art technology uses triarylamine-based materials to satisfy many of the current luminescent and phosphorescent OLED designs. Problems with current OLEDs include fast aging/short life span, undesirably high operating voltages, low efficiency and low levels of brightness. There remains a need for new HTL materials for OLED applications.

SUMMARY OF INVENTION

The invention provides a composition comprising a compound of Structure 1:

wherein $R_1$ through $R_{24}$ are each, independently, selected from the following: a hydrogen, a hydrocarbyl, a substituted hydrocarbyl, a cyano, an alkoxy, an aryloxy, or a $NR'_2$ wherein R' is selected from an aryl or a heteroaryl; and wherein, optionally, two or more of $R_1$ to $R_{24}$ form one or more ring structures; and wherein Z is selected from group (1) or (2):

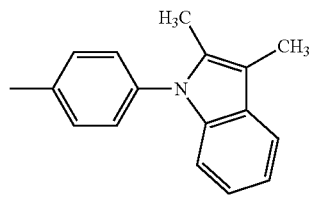

(1)

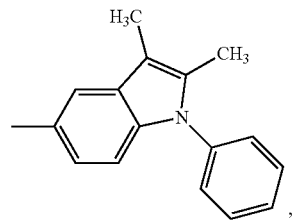

(2)

and wherein, optionally, one or more hydrogens may be substituted with deuterium.

The invention further provides a film formed from a composition comprising at least one compound of Structure 1, and an electronic device comprising at least one component formed from a composition or from a film comprising at least one compound of Structure 1.

The invention also provides a composition comprising a compound of Structure 2:

(Structure 1)

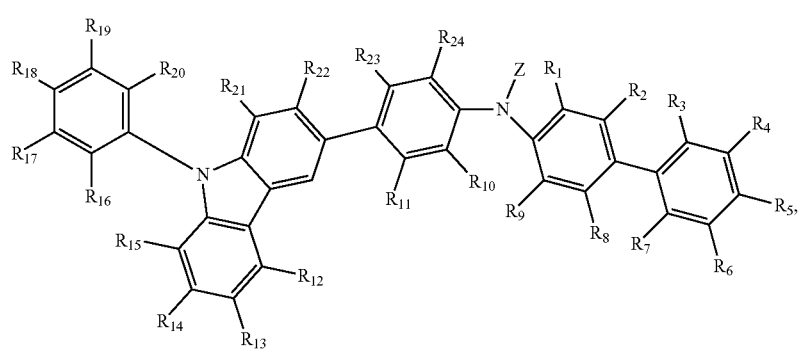

(Structure 2)

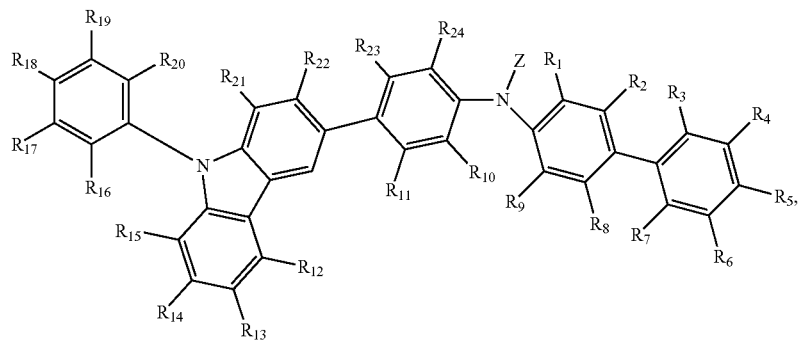

wherein $R_1$ through $R_{24}$ are each, independently, selected from the following: a hydrogen, a hydrocarbyl, a substituted hydrocarbyl, a cyano, an alkoxy, an aryloxy, or a $NR'_2$ wherein R' is selected from an aryl or a heteroaryl; and wherein, optionally, two or more of $R_1$ to $R_{24}$ form one or more ring structures; and wherein Z is selected from group (1a) or (2a):

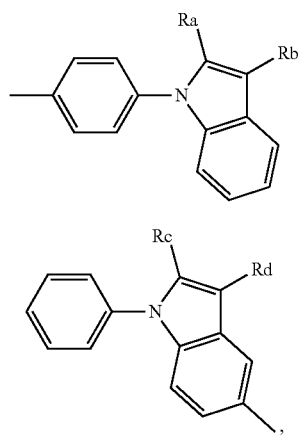

wherein, optionally, one or more hydrogens may be substituted with deuterium.

BRIEF DESCRIPTION OF THE DRAWINGS

FIG. 1 depicts the cyclic voltammetry profiles of a model compound (9-(4-(2,3-dimethyl-1H-indol-1-yl)phenyl)-9H-carbazole), used to determine the stability of the Z moiety, as noted in the "stability study" below.

DETAILED DESCRIPTION OF THE INVENTION

Overview

A new class of 2,3-disubstituted indole compounds have been discovered that are highly stable and useful in OLEDs and other electroluminescent (EL) display devices, particularly as charge transport materials (e.g., HTL and ETL materials). Electroluminescent (EL) display devices incorporating these compounds exhibit good electroluminescent performance.

Embodiments

In a first aspect, the present disclosure provides a composition comprising a compound selected from Structure 1:

(Structure 1)

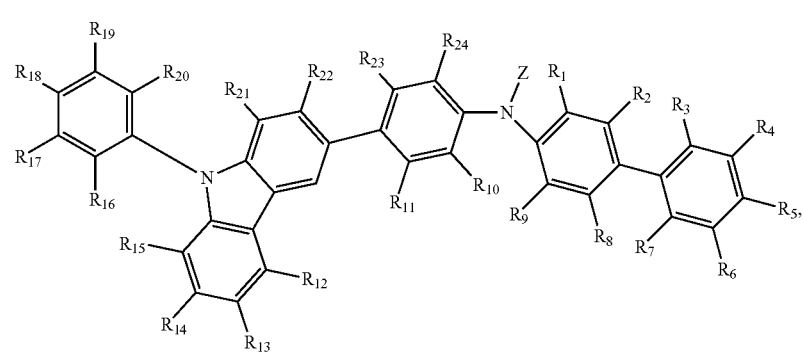

wherein for group 1a, Ra and Rb are each independently an alkyl, and wherein at least one of Ra and/or Rb comprises at least two carbon atoms; and for group 2a, Rc and Rd are each independently an alkyl, and wherein at least one of Rc and/or Rd comprises at least two carbon atoms; and wherein $R_1$ through $R_{24}$ are each, independently, selected from a hydrogen, a hydrocarbyl, a substituted hydrocarbyl, a cyano, an alkoxy, an aryloxy, and a $NR'_2$ wherein R' is selected from an aryl or a heteroaryl; and wherein, optionally, two or more of $R_1$ to $R_{24}$ form one or more ring structures; and wherein Z is selected from group (1) or (2):

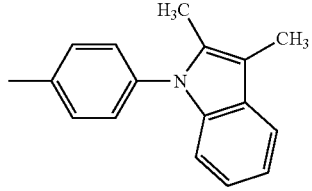
(1)

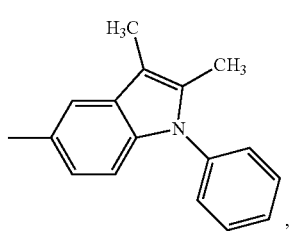
(2)

and wherein, optionally, one or more hydrogens may be substituted with deuterium.

The compound of Structure 1 can comprise a combination of two or more embodiments as described herein.

An inventive composition may comprise a combination of two or more embodiments described herein.

As used herein $R1=R_1$, $R2=R_2$, $R3=R_3$, and so forth. As used herein $NR'2=NR'_2$.

In one embodiment, for Structure 1, R1 through R24 are each, independently, selected from a hydrogen, a C1-C20 hydrocarbyl, a substituted C1-C20 hydrocarbyl, a cyano, a C1-C20 alkoxy, a C6-C18 aryloxy, or an $NR'_2$ group with the R' group selected from a C6-C18 aryl or a C3-C18 heteroaryl.

In one embodiment, $R_1$ through $R_{24}$ are each independently selected from the following: hydrogen, an unsubstituted hydrocarbyl, or a substituted hydrocarbyl.

In one embodiment, for Structure 1, R1 through R24 are each, independently, hydrogen.

In one embodiment, for Structure 1, two or more R groups (R1 through R24) do not form one or more ring structures.

In one embodiment, for Structure 1, one or more hydrogens are not substituted with deuterium.

In one embodiment, for Structure 1, the Z is group (1):

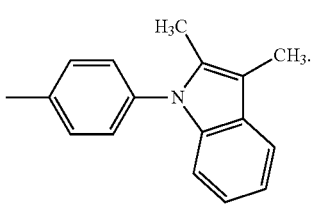
(1)

In one embodiment, Structure 1 is Structure 1a:

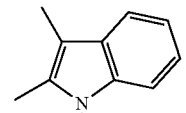
(Structure 1a)

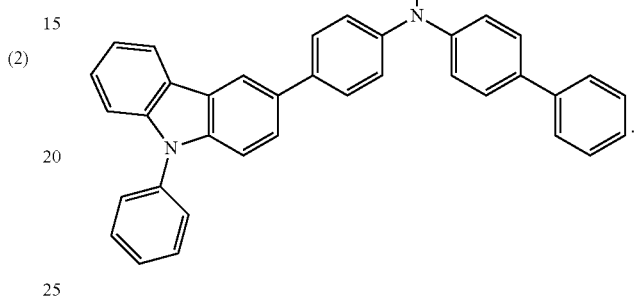

In one embodiment, for Structure 1, Z is group (2):

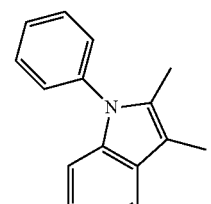
(2)

In one embodiment, Structure 1 is Structure 2a:

(Structure 2a)

In one embodiment, the compound of Structure 1 comprises at least one deuterium atom.

In one embodiment, the compound of Structure 1 does not comprise a deuterium atom.

In one embodiment, the compound of Structure 1 has a purity greater than 99 percent (%) as determined by analytical methods, for example, high-performance liquid chromatography (HPLC), liquid chromatography (LC), and/or liquid chromatography-mass spectrometry (LC-MS or HPLC-MS).

In one embodiment, the compound of Structure 1 has a glass transition temperature (Tg) from 90 to 200° C., further from 100 to 180° C., further from 110 to 180° C., as determined by DSC.

In one embodiment, the compound of Structure 1 has a molecular weight of 600 grams/mole (g/mole) to 1000 g/mole, further from 600 to 900 g/mole, further from 700 to 900 g/mole.

In one embodiment, the compound of Structure 1 has a highest occupied molecular orbital (HOMO) level of from −4.40 eV to −5.00 eV, further from −4.50 eV to −4.90 eV.

In one embodiment, the compound of Structure 1 has a lowest unoccupied molecular orbital (LUMO) level from −1.00 eV to 0.00 eV, further from −0.90 eV to −0.20 eV, further from −0.90 eV to −0.40 eV.

In one embodiment, the compound of Structure 1 has a triplet energy level from 2.50 eV to 3.00 eV, further from 2.55 eV to 2.90 eV, further 2.60 eV to 2.80 eV.

In one embodiment, the composition comprises at least two compounds of Structure 1.

In an embodiment, the composition comprises at least one compound of Structure 1 in which Z is group (1) and at least one compound of Structure 1 in which Z is group (2).

In one embodiment, the composition consists essentially of a compound of Structure 1 in which Z is group (1).

In one embodiment, the composition consists essentially of a compound of Structure 1 in which Z is group (2).

In one embodiment, for Structure 1, the Z group of group 1, when attached to a carbazole via the nitrogen atom of the carbazole, provides an electrochemical stability within $\pm 3.0 \times 10^{-5}$ A, for at least 2, further at least 3, further at least 4, and further at least 5 repeated cyclic voltammograms, each with a voltage range from 1.6 V to 0 V. Thus, for the respective number of cyclic voltammograms (or cyclic voltammetry profiles), the difference in amperage (A) between each voltage point (V), for any two voltammograms (or profiles), is within $\pm 3.0 \times 10^{-5}$ A. See the experimental section below for a representative cyclic voltammetry measurement, and FIG. 1 for representative cyclic voltammograms (or cyclic voltammetry profiles).

In one embodiment, for Structure 1, the Z group of group 1, when attached to a carbazole via the nitrogen atom of the carbazole, provides an electrochemical stability within $\pm 2.5 \times 10^{-5}$ A, for at least 2, further at least 3, further at least 4, and further at least 5 repeated cyclic voltammograms, each with a voltage range from 1.6 V to 0 V.

In one embodiment, for Structure 1, the Z group of group 1, when attached to a carbazole via the nitrogen atom of the carbazole, provides an electrochemical stability within $\pm 2.0 \times 10^{-5}$ A, for at least 2, further at least 3, further at least 4, and further at least 5 repeated cyclic voltammograms, each with a voltage range from 1.6 V to 0 V.

In one embodiment, for Structure 1, the Z group of group 1, when attached to a carbazole via the nitrogen atom of the carbazole, provides an electrochemical stability within $\pm 1.5 \times 10^{-5}$ A, for at least 2, further at least 3, further at least 4, and further at least 5 repeated cyclic voltammograms, each with a voltage range from 1.6 V to 0 V.

In one embodiment, for Structure 1, the Z group of group 1, when attached to a carbazole via the nitrogen atom of the carbazole, provides an electrochemical stability within $\pm 1.0 \times 10^{-5}$ A, for at least 2, further at least 3, further at least 4, and further at least 5 repeated cyclic voltammograms, each with a voltage range from 1.6 V to 0 V.

In one embodiment, the composition is 100 weight percent (wt %) of the compound of Structure 1, based on the weight of the composition. In a further embodiment, the composition comprises from 10 to 99 wt % of the compound of Structure 1, based on the weight of the composition. In a further embodiment, the composition comprises from 50 to 99 wt %, further from 70 to 99 wt %, further from 80 to 99 wt %, further from 90 to 99 wt %, of the compound of Structure 1, based on the weight of the composition.

The inventive composition can comprise a combination of two or more embodiments as described herein.

In a second aspect, the present disclosure also provides an inventive film comprising at least one layer formed from an inventive composition comprising a compound of Structure 1, including an inventive composition of one or more embodiments described herein.

In one embodiment, the film comprises at least two layers, A and B, wherein the Layer A is formed from a composition A comprising a compound of Structure 1.

In one embodiment, the Layer A formed from the inventive composition can comprise a combination of two or more embodiments described herein.

In one embodiment, the Layer A is in contact with the Layer B.

In one embodiment, the thickness of Layer A is from 5 nm to 500 nm, or from 5 nm to 100 nm, or from 5 nm to 50 nm.

In one embodiment, the Layer A is a hole transport layer (HTL).

In one embodiment, the Layer A is a hole transport layer (HTL) formed from a composition comprising a compound of Structure 1, which compound is a hole transport layer (HTL) compound. Generally, an HTL compound is a material that transports holes. An HTL compound of Structure 1 should desirably have a larger triplet energy than the EML layer to block excitors migration from an adjacent emitting material layer (EML).

In one embodiment, the inventive composition can comprise 100 wt % of a hole transport layer (HTL) compound of Structure 1, based on the weight of the composition.

In one embodiment, the inventive composition comprising a hole transport layer (HTL) compound of Structure 1 can comprise a combination of two or more embodiments described herein.

In one embodiment, the inventive film is formed from casting from a solution.

In one embodiment, the inventive film is formed by deposition from an evaporation process or a sublimation process in a vacuum.

In one embodiment, the film comprises a hole transport layer (HTL) as Layer A and one or more additional layers selected from a hole injection layer (HIL), an emitting material layer (EML), an electron transport layer (ETL), or an electron injection layer (EIL).

In one embodiment, each film layer is formed from casting from a solution.

In one embodiment, each film layer is formed by deposition from an evaporation process or a sublimation process in a vacuum.

An inventive film can comprise a combination of two or more embodiments described herein.

In another aspect, the present disclosure also provides an electronic device comprising at least one component formed from an inventive composition, including an inventive composition of one or more embodiments described herein.

The present disclosure also provides an electronic device comprising at least one component formed from an inventive film, including an inventive film of one or more embodiments described herein.

In one embodiment, the device is a light-emitting or electroluminescent (EL) device.

vidual layers of OLEDs, including HIL (hole injection layers), HTL (hole transport layers), EML (emissive layers, including host and dopant), EIL (electron injection layers), and ETL (electron transport layers).

The invention also provides A composition comprising a compound of Structure 2:

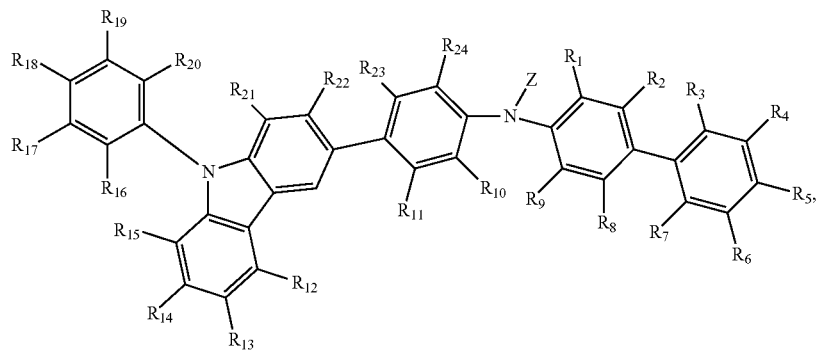

(Structure 2)

In one embodiment, the electronic device comprises an organic material layer disposed between first and second electrodes (e.g., anode and cathode).

In one embodiment, the electronic device comprises at least one component formed from the inventive composition.

In one embodiment, the electronic device comprises an organic Layer A formed from the inventive composition disposed between first and second electrodes.

In one embodiment, the electronic device further comprises a second Layer B.

In one embodiment, the Layer A is in contact with the Layer B.

In one embodiment, the Layer A of the electronic device is a hole transport layer (HTL).

In one embodiment, the organic material layer of the electronic device comprises at least one of an HIL (hole injection layer), an HTL (hole transport layer), an EML (emissive material layer), and an ETL (electron transport layer).

In an embodiment, the organic material layer further includes a hole-blocking layer to improve efficiency of phosphorescent emitter devices.

In one embodiment, the electronic device is an organic light emitting diode (OLED).

In one embodiment, the electronic device is an OLED comprising an organic material layer comprising an inventive film disposed between two electrodes (anode and cathode).

In one embodiment, the OLED device comprises a multi-layered organic material layer with one or more layers selected from an HIL (hole injection layer), an HTL (hole transport layer), an EML (emissive layer), an ETL (electron transport layer), or an EIL (electron injection layer), of which at least one layer is formed from an inventive composition comprising a compound of Structure 1.

An inventive device may comprise a combination of two or more embodiments as described herein.

The inventive compositions are useful for application in organic light emitting diodes (OLED) or related organic electronic devices, including organic solar cells. More specifically, the invented compositions find application in indiwherein $R_1$ through $R_{24}$ are each, independently, selected from the following: a hydrogen, a hydrocarbyl, a substituted hydrocarbyl, a cyano, an alkoxy, an aryloxy, or a $NR'_2$ wherein R' is selected from an aryl or a heteroaryl; and wherein, optionally, two or more of $R_1$ to $R_{24}$ form one or more ring structures; and wherein Z is selected from group (1a) or (2a):

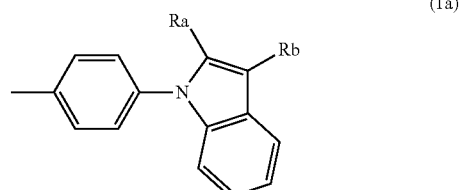

(1a)

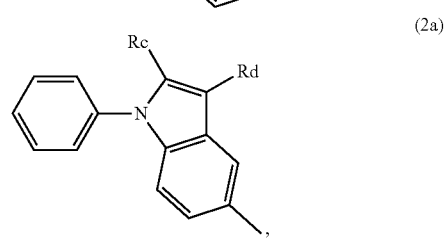

(2a)

wherein for group 1a, Ra and Rb are each independently an alkyl, and at least one of Ra and/or Rb comprises at least two carbon atoms; and for group 2a, Rc and Rd are each independently an alkyl, and wherein at least one of Ra and/or Rb comprises at least two carbon atoms; and wherein, optionally, one or more hydrogens may be substituted with deuterium.

In one embodiment, for Structure 2, Ra=Rb and Rc=Rd.

In one embodiment, for Structure 2, each of Ra and Rb, independently is a C2-C6 alkyl, further a C2-C5 alkyl and further a C2-C4 alkyl; and each of Rc and Rd, independently is a C2-C6 alkyl, further a C2-C5 alkyl and further a C2-C4 alkyl.

In one embodiment, the compound of Structure 2 comprises at least one deuterium atom.

In one embodiment, the compound of Structure 2 does not comprise a deuterium atom.

In one embodiment, the compound of Structure 2 has a purity greater than 99 percent (%) as determined by analytical methods, for example, high-performance liquid chromatography (HPLC), liquid chromatography (LC), and/or liquid chromatography-mass spectrometry (LC-MS or HPLC-MS).

In one embodiment, the compound of Structure 2 has a glass transition temperature (Tg) from 90 to 200° C., further from 100 to 180° C., further from 110 to 180° C., as determined by DSC.

In one embodiment, the compound of Structure 2 has a molecular weight of 600 grams/mole (g/mole) to 1000 g/mole, further from 600 to 900 g/mole, further from 700 to 900 g/mole.

In one embodiment, the compound of Structure 2 has a highest occupied molecular orbital (HOMO) level of from −4.40 eV to −5.00 eV, further from −4.50 eV to −4.90 eV.

In one embodiment, the compound of Structure 2 has a lowest unoccupied molecular orbital (LUMO) level from −1.00 eV to 0.00 eV, further from −0.90 eV to −0.20 eV, further from −0.90 eV to −0.40 eV.

In one embodiment, the compound of Structure 2 has a triplet energy level from 2.50 eV to 3.00 eV, further from 2.55 eV to 2.90 eV, further 2.60 eV to 2.80 eV.

In one embodiment, the composition comprises at least two compounds of Structure 2.

In one embodiment, the composition comprises a compound of Structure 2 and a compound of Structure 1.

In an embodiment, the composition comprises at least one compound of Structure 2 in which Z is group (1a) and at least one compound of Structure 2 in which Z is group (2a).

In one embodiment, the composition consists essentially of a compound of Structure 2 in which Z is group (1a).

In one embodiment, the composition consists essentially of a compound of Structure 2 in which Z is group (2a).

In one embodiment, the composition is 100 weight percent (wt %) of the compound of Structure 2, based on the weight of the composition. In a further embodiment, the composition comprises from 10 to 99 wt % of the compound of Structure 2, based on the weight of the composition. In a further embodiment, the composition comprises from 50 to 99 wt %, further from 70 to 99 wt %, further from 80 to 99 wt %, further from 90 to 99 wt %, of the compound of Structure 2, based on the weight of the composition.

The inventive composition can comprise a combination of two or more embodiments as described herein.

In a second aspect, the present disclosure also provides an inventive film comprising at least one layer formed from an inventive composition comprising a compound of Structure 2, including an inventive composition of one or more embodiments described herein.

In one embodiment, the film comprises at least two layers, C and D, wherein the Layer C is formed from a composition C comprising a compound of Structure 2.

In one embodiment, the Layer C formed from the inventive composition can comprise a combination of two or more embodiments described herein.

In one embodiment, the Layer C is in contact with the Layer D.

In one embodiment, the thickness of Layer C is from 5 nm to 500 nm, or from 5 nm to 100 nm, or from 5 nm to 50 nm.

In one embodiment, the Layer C is a hole transport layer (HTL).

In one embodiment, the Layer C is a hole transport layer (HTL) formed from a composition comprising a compound of Structure 2, which compound is a hole transport layer (HTL) compound. Generally, an HTL compound is a material that transports holes. An HTL compound of Structure 2 should desirably have a larger triplet energy than the EML layer to block excitors migration from an adjacent emitting material layer (EML).

In one embodiment, the inventive composition can comprise 100 wt % of a hole transport layer (HTL) compound of Structure 2, based on the weight of the composition.

In one embodiment, the inventive composition comprising a hole transport layer (HTL) compound of Structure 2 can comprise a combination of two or more embodiments described herein.

In one embodiment, the inventive film is formed from casting from a solution.

In one embodiment, the inventive film is formed by deposition from an evaporation process or a sublimation process in a vacuum.

In one embodiment, the film comprises a hole transport layer (HTL) as Layer C and one or more additional layers selected from a hole injection layer (HIL), an emitting material layer (EML), an electron transport layer (ETL), or an electron injection layer (EIL).

In one embodiment, each film layer is formed from casting from a solution.

In one embodiment, each film layer is formed by deposition from an evaporation process or a sublimation process in a vacuum.

An inventive film can comprise a combination of two or more embodiments described herein.

In another aspect, the present disclosure also provides an electronic device comprising at least one component formed from an inventive composition, including an inventive composition of one or more embodiments described herein.

The present disclosure also provides an electronic device comprising at least one component formed from an inventive film, including an inventive film of one or more embodiments described herein.

In one embodiment, the device is a light-emitting or electroluminescent (EL) device.

In one embodiment, the electronic device comprises an organic material layer disposed between first and second electrodes (e.g., anode and cathode).

In one embodiment, the electronic device comprises at least one component formed from the inventive composition.

In one embodiment, the electronic device comprises an organic Layer C formed from the inventive composition disposed between first and second electrodes.

In one embodiment, the electronic device further comprises a second Layer D.

In one embodiment, the Layer C is in contact with the Layer D.

In one embodiment, the Layer C of the electronic device is a hole transport layer (HTL).

In one embodiment, the organic material layer of the electronic device comprises at least one of an HIL (hole injection layer), an HTL (hole transport layer), an EML (emissive material layer), and an ETL (electron transport layer).

In an embodiment, the organic material layer further includes a hole-blocking layer to improve efficiency of phosphorescent emitter devices.

In one embodiment, the electronic device is an organic light emitting diode (OLED).

In one embodiment, the electronic device is an OLED comprising an organic material layer comprising an inventive film disposed between two electrodes (anode and cathode).

In one embodiment, the OLED device comprises a multi-layered organic material layer with one or more layers selected from an HIL (hole injection layer), an HTL (hole transport layer), an EML (emissive layer), an ETL (electron transport layer), or an EIL (electron injection layer), of which at least one layer is formed from an inventive composition comprising a compound of Structure 2.

An inventive device may comprise a combination of two or more embodiments as described herein.

The inventive compositions are useful for application in organic light emitting diodes (OLED) or related organic electronic devices, including organic solar cells. More specifically, the invented compositions find application in individual layers of OLEDs, including HIL (hole injection layers), HTL (hole transport layers), EML (emissive layers, including host and dopant), EIL (electron injection layers), and ETL (electron transport layers)

Definitions

Unless stated to the contrary, implicit from the context, or customary in the art, all parts and percents are based on weight. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

The numerical ranges disclosed herein include all values from, and including, the lower value and the upper value. For ranges containing explicit values (e.g., 1 or 2, or 3 to 5, or 6, or 7) any subrange between any two explicit values is included (e.g., 1 to 2; 2 to 6; 5 to 7; 3 to 7; 5 to 6; etc.).

The terms "comprising," "including," "having," and their derivatives, are not intended to exclude the presence of any additional component, step or procedure, whether or not the same is specifically disclosed. In order to avoid any doubt, all compositions claimed through use of the term "comprising" may include any additional additive, adjuvant or compound, whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed.

The term "hydrocarbon," as used herein, refers to a chemical group containing only hydrogen atoms and carbon atoms. The term "hydrocarbyl", as used herein, refers to a univalent group formed by removing a hydrogen from a hydrocarbon, such as, for example, ethyl, methyl or phenyl. The term "substituted hydrocarbon," (or "substituted hydrocarbyl"), as used herein, refers to a hydrocarbon (or hydrocarbyl) in which at least one hydrogen atom is substituted with a substituent comprising at least one heteroatom. Heteroatoms include, but are not limited to, a halide, O, N, P and S. Substituents include, but are not limited to, halide, OR', NR'$_2$, PR'$_2$, P(=O)R'$_2$, and SiR'$_3$, where each R' is independently a C$_1$-C$_{20}$ hydrocarbyl group. An "unsubstituted hydrocarbon" (or "unsubstituted hydrocarbyl") is a hydrocarbon (or hydrocarbyl) that contains no heteroatoms.

The term "alkoxy," as used herein, refers to an alkyl in which at least one hydrogen atom is substituted with an oxygen atom, O.

The term "alkyl," as used herein, refers to an organic radical derived from an aliphatic hydrocarbon by deleting one hydrogen atom therefrom. An alkyl group can be a linear, branched, cyclic or a combination thereof.

The term "substituted alkyl," as used herein, refers to an alkyl, in which at least one hydrogen atom is substituted with a substituent that comprises at least one heteroatom. Heteroatoms include, but are not limited to, O, N, P and S. Substituents include, but are not limited to, halide, OR', NR'$_2$, PR'$_2$, P(=O)R'$_2$, SiR'$_3$, where each R' is independently a C$_1$-C$_{20}$ hydrocarbyl group.

The term "aryl," as used herein, refers to an organic radical derived from aromatic hydrocarbon by deleting one hydrogen atom therefrom. An aryl group may be a monocyclic and/or fused ring system, each ring of which suitably contains from 5 to 7, preferably from 5 or 6 atoms. Structures wherein two or more aryl groups are combined through single bond(s) are also included. Specific examples include, but are not limited to, phenyl, tolyl, naphthyl, biphenyl, anthryl, indenyl, fluorenyl, 9,9-dimethylfluorenyl, benzofluorenyl, phenanthryl, triphenylenyl, pyrenyl, perylenyl, chrysenyl, naphtacenyl, fluoranthenyl, and the like. The naphthyl may be 1-naphthyl or 2-naphthyl, the anthryl may be 1-anthryl, 2-anthryl or 9-anthryl, and the fluorenyl may be any one of 1-fluorenyl, 2-fluorenyl, 3-fluorenyl, 4-fluorenyl and 9-fluorenyl.

The term "substituted aryl," as used herein, refers to an aryl, in which at least one hydrogen atom is substituted with a substituent comprising at least one heteroatom. Heteroatoms include, but are not limited to, O, N, P and S. Substituents include, but are not limited to, halide OR', NR'$_2$, PR'$_2$, P(=O)R'$_2$, and SiR'$_3$, where each R' is independently a C$_1$-C$_{20}$ hydrocarbyl group.

The term "aryloxy," as used herein, refers to an aryl group in which at least one hydrogen atom is replaced with an oxygen atom, O. such as a phenoxy group (C$_6$H$_5$O—).

The term "cyano," as used herein, refers to a radical group with the molecular formula.CN, which consists of a carbon atom triple-bonded to a nitrogen atom.

The term "heteroalkyl," as used herein, refers to an alkyl group, in which at least one carbon atom or CH group or CH$_2$ is substituted with a heteroatom or a chemical group containing at least one heteroatom. Heteroatoms include, but are not limited to, O, N, P and S. A heteroalkyl group may be a linear, branched, cyclic or a combination thereof.

The term "substituted heteroalkyl," as used herein, refers to an heteroalkyl, in which at least one hydrogen atom is substituted with a substituent that comprises at least one heteroatom. Heteroatoms include, but are not limited to, O, N, P and S. Substituents include, but are not limited to, halide, OR', NR'$_2$, PR'$_2$, P(=O)R'$_2$, and SiR'$_3$, where each R' is independently a C$_1$-C$_{20}$ hydrocarbyl group.

The term "heteroaryl," as used herein, refers to an aryl group, in which at least one carbon atom or CH group or CH$_2$ is substituted with a heteroatom or a chemical group containing at least one heteroatom. Heteroatoms include, but are not limited to, O, N, P and S. The heteroaryl may be a 5- or 6-membered monocyclic heteroaryl or a polycyclic heteroaryl which is fused with one or more benzene ring(s), and may be partially saturated. The structures having one or more heteroaryl group(s) bonded through a single bond are also included. The heteroaryl groups may include divalent aryl groups of which the heteroatoms are oxidized or quarternized to form N-oxides, quaternary salts, and the like.

Specific examples include, but are not limited to, monocyclic heteroaryl groups, such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl; polycyclic heteroaryl groups, such as benzofuranyl, fluoreno[4, 3-b]benzofuranyl, benzothiophenyl, fluoreno[4, 3-13]benzothiophenyl, isobenzofuranyl, benzimidazolyl, benzothiazolyl, benzisothiazolyl, benzisoxazolyl, benzoxazolyl, isoindolyl, indolyl, indazolyl, benzothia-diazolyl, quinolyl, isoquinolyl, cinnolinyl, quinazolinyl, quinoxalinyl, carbazolyl, phenanthridinyl and benzodioxolyl, and corresponding N-oxides (for example, pyridyl N-oxide, quinolyl N-oxide) and quaternary salts thereof.

The term "substituted heteroaryl," as used herein, refers to a heteroaryl in which at least one hydrogen atom is substituted with a substituent comprising at least one heteroatom, and any combination thereof. Heteroatoms include, but are not limited to, O, N, P and S. Substituents include, but are not limited to, halide OR', $NR'_2$, $PR'_2$, $P(=O)R'_2$, and $SiR'_3$, where each R' is independently a $C_1$-$C_{20}$ hydrocarbyl group. A "heteroatom" is an atom other than carbon or hydrogen. Nonlimiting examples of heteroatoms include: F, Cl, Br, N, O, P, B, S, Si, Sb, Al, Sn, As, Se and Ge.

The term "ring structure," as used herein, refers to a ring composed of a hydrocarbon or a substituted hydrocarbon. A ring structure can be saturated or unsaturated, and can contain one or two or more rings.

The term "anode," as used herein, refers to a layer in an electroluminescent (EL) device that is capable of injecting positive charges (holes) into a hole injection layer (HIL) and/or hole transporting layer (HTL), positioned thereon, when a current flows through the device. The anode is typically disposed on a substrate, as for example, a silicon wafer, a quartz or glass plate, a metal plate, a plastic film or sheet. Examples of anode materials include metals (e.g., vanadium, chromium, copper, zinc, gold) or alloys thereof, metal oxides (e.g., zinc oxide, indium oxide), metal halides, electroconductive polymers (e.g., polypyrole, polyaniline), and combinations thereof. An optically transparent anode can be formed, for example, from a transparent conductive oxide such as indium-tin-oxide (ITO) or indium zinc oxide (IZO).

The term "cathode," as used herein, refers to a layer in an electroluminescent (EL) device that is capable of injecting negative charges (electrons) into an electron injection layer (EIL) and/or electron transporting layer (ETL), positioned on the electron injection layer (EIL), when a current flows through the device. The cathode can be formed, for example, from metals such as tin, magnesium, indium, calcium, sodium, lithium, aluminum, silver, or alloys thereof. An optically transparent cathode can be formed, for example, from a transparent conductive oxide such as indium-tin-oxide (ITO) or indium zinc oxide (IZO).

The term "dopant" and like terms, as described herein, refer to a material that is added to an organic emissive layer, as an additive, and undergoes radiative emission from an excited state. The excited state can be generated by application of electrical current in an electroluminescent device.

The term "electron injection layer," or "EIL," as used herein, refers to a layer in an electroluminescent (EL) device that is positioned between the cathode and an electron transport layer (ETL), and functions to inject electrons from the cathode into the ETL layer. The EIL layer can be formed, for example, from a metal complex compound, such as metal chelated oxinoid compounds, triazines, and hydroxyquinoline derivatives, among others.

The term "electron transport layer," or "ETL," as used herein, refers to a layer in an electroluminescent (EL) device that is positioned between an electron injection layer (EIL) and an emitting material layer (EML), and functions to transport electrons injected from a cathode to the emitting material layer. The ETL layer is composed of a material having a high electron affinity, a high electron mobility, and a high electron stability. The ETL layer can be formed, for example, from anthracene-based, pyridine-based, pyrimidine-based, quinazoline-based and triazine-based compounds, among others.

The term "emitting material layer" or "EML," and like terms, as used herein, refer to a layer in an electroluminescent (EL) device that is made of a material having a high quantum efficiency, and, in which holes and electrons that are injected from an anode and a cathode, respectively, are recombined so as to emit light in a visible range. The EML layer is typically positioned between a hole transport layer (HTL) and an electron transport layer (ETL). The EML layer can be formed, for example, from a luminescent fluorescent material or a luminescent phosphorescent material, which can produce electroluminescence as a result of electron-hole pair recombination in the EML layer. The EML layer can be composed of a host material doped with an emitting material (dopant), where light emission comes from the dopant material, for example, a fluorescent compound or phosphorescent compound. The compound for the EML layer (host plus dopant) generates visible light colors.

"Hole injection layer," or "HIL," and like terms, refers to a layer in an electroluminescent (EL) device, which functions to transports holes from the anode to the hole transport layer (HTL) or emitting material layer (EML). The hole injection layer is typically formed, on the anode, from an aromatic amine or diamine.

"Hole transport layer", or "HTL", and like terms, refers to a layer in an electroluminescent (EL) device, which is made from a material that transports holes. Typically, the HTL compound has high hole mobility, and the appropriate ionization potential to provide a small energy barrier for the following: hole injection from the anode or hole injection layer (HIL), and hole injection into the emitting material layer (EML), each leading to reduced operating voltage in the device. The HTL compound is also used to help block passage of electrons transported by the emitting material layer (EML). Small electron affinity is typically required to block electrons. An HTL compound (e.g., of Structure 1) should desirably have a larger triplet energy to block exciton migration from an adjacent emitting material layer (EML). Examples of conventional HTL compounds include aromatic tertiary amines (e.g., an arylamine), for example, di(p-tolyl)aminophenyl]cyclohexane (TPAC), N,N-diphenyl-N,N-bis(3-methylphenyl)-1,1-biphenyl-4,4-diamine (TPD), and N,N'-diphenyl-N,N '-bis(1-naphthyl)-(1,1'-biphenyl)-4,4'-diamine (NPB), among others The term "substrate," as used herein, refers to a support for an electroluminescent (EL) device (e.g., an OLED). Nonlimiting examples of substrates include a silicon wafer, a quartz or glass plate, a metal plate, a metal foil, a plastic film or sheet (e.g., a polymeric resins such as polyester, polymethacrylate, polycarbonate, polysulfone, among others).

EXAMPLES

Reagents and Test Methods

All solvents and reagents were obtained from commercial vendors, including Sigma-Aldrich, TCI, and Alfa Aesar, and were used in the highest available purities, and/or when necessary, recrystallized before use. Dry solvents were obtained from in-house purification/dispensing system (hexane, toluene, and tetrahydrofuran), or purchased from Sigma-Aldrich. All experiments involving "water sensitive compounds" were conducted in "oven dried" glassware, under nitrogen atmosphere, or in a glovebox. Reactions were monitored by analytical, thin-layer chromatography (TLC) on precoated glass plates (VWR 60 F254), and visualized by UV light and/or potassium permanganate staining. Flash chromatography was performed on an ISCO COMBI-FLASH system with GRACERESOLV cartridges. GC-mass spectrometry (GC-MS) was performed on a HP 6890 series GC system with a "12 m×0.2 mm×0.55 µM" DB-MS column (coiled).

$^1$H-NMR-spectra (500 MHz or 400 MHz) were obtained on a Varian VNMRS-500 or a VNMRS-400 spectrometer, at 30° C., unless otherwise noted. The chemical shifts were referenced to TMS (δ=0.00) in CDCl$_3$.

$^{13}$C-NMR spectra (125 MHz or 100 MHz) were obtained on a Varian VNMRS-500 or a VNRMS-400 spectrometer, and referenced to TMS (δ=0.00) in CDCl$_3$.

Routine LC/MS studies were carried out as follows. Five microliter aliquots of the sample, as "3 mg/ml solution in THF," were injected on an AGILENT 1200SL binary gradient, liquid chromatography, coupled to an AGILENT 6520 QTof, quadruple-time of flight MS system, via a dual spray electrospray (ESI) interface, operating in the PI mode. The following analysis conditions were used: column: 150×4.6 mm ID, 3.5 µm ZORBAX SB-C8; column temperature: 40° C.; mobile phase: 75/25 A/B to 15/85 A/B at 40 minutes; solvent A=0.1 v % formic acid in water; solvent B=THF; flow 1.0 mL/min; UV detection: diode array 210 to 600 nm (extracted wavelength 250,280 nm); ESI conditions: gas temperature 365° C.; gas flow—8 ml/min; capillary—3.5 kV; nebulizer—40PSI; fragmentor—145V.

DSC was done using a 2000 instrument at a scan rate of 10° C./min, and in a nitrogen atmosphere for all cycles. The sample (about 7-10 mg) was scanned from room temperature to 300° C., cooled to −60° C., and reheated to 300° C. The glass transition temperature ($T_g$) was measured on the second heating scan. Data analysis was performed using TA Universal Analysis software. The $T_g$ was calculated using the "mid-point of inflection" methodology.

Modeling

All computations utilized the Gaussian 09 program[1]. The calculations were performed with the hybrid density functional theory (DFT) method, B3LYP,[2] and the 6-31G* (5d) basis set.[3] The singlet state calculations used the closed shell approximation, and the triplet state calculations used the open shell approximation. All values are quoted in electronvolts (eV). The HOMO and LUMO values were determined from the orbital energies of the optimized geometry of the singlet ground state. The Triplet Energies ($T_1$) were determined as the difference between the total energy of the optimized triplet state and the optimized singlet state.

[1] Gaussian 09, Revision A.02, Frisch, M. J.; Trucks, G. W.; Schlegel, H. B.; Scuseria, G. E.; Robb, M. A.; Cheeseman, J. R.; Scalmani, G.; Barone, V.; Mennucci, B.; Petersson, G. A.; Nakatsuji, H.; Caricato, M.; Li, X.; Hratchian, H. P.; Izmaylov, A. F.; Bloino, J.; Zheng, G.; Sonnenberg, J. L.; Hada, M.; Ehara, M.; Toyota, K.; Fukuda, R.; Hasegawa, J.; Ishida, M.; Nakajima, T.; Honda, Y.; Kitao, O.; Nakai, H.; Vreven, T.; Montgomery, Jr., J. A.; Peralta, J. E.; Ogliaro, F.; Bearpark, M.; Heyd, J. J.; Brothers, E.; Kudin, K. N.; Staroverov, V. N.; Kobayashi, R.; Normand, J.; Raghavachari, K.; Rendell, A.; Burant, J. C.; Iyengar, S. S.; Tomasi, J.; Cossi, M.; Rega, N.; Millam, J. M.; Klene, M.; Knox, J. E.; Cross, J. B.; Bakken, V.; Adamo, C.; Jaramillo, J.; Gomperts, R.; Stratmann, R. E.; Yazyev, O.; Austin, A. J.; Cammi, R.; Pomelli, C.; Ochterski, J. W.; Martin, R. L.; Morokuma, K.; Zakrzewski, V. G.; Voth, G. A.; Salvador, P.; Dannenberg, J. J.; Dapprich, S.; Daniels, A. D.; Farkas, O.; Foresman, J. B.; Ortiz, J. V.; Cioslowski, J.; Fox, D. J., Gaussian, Inc., Wallingford Conn., 2009.

[2] (a) Becke, A. D. *J. Chem. Phys.* 1993, 98, 5648. (b) Lee, C.; Yang, W.; Pan, R. G. *Phys. Rev B* 1988, 37, 785. (c) Miehlich, B.; Savin, A.; Stoll, H.; Preuss, H. *Chem. Phys. Lett.* 1989, 157, 200.

[3] (a) Ditchfield, R.; Hehre, W. J.; Pople, J. A. *J. Chem. Phys.* 1971, 54, 724. (b) Hehre, W. J.; Ditchfield, R.; Pople, J. A. *J. Chem. Phys.* 1972, 56, 2257. (c) Gordon, M. S. *Chem. Phys. Lett.* 1980, 76, 163.

Table 1 lists the electronic properties (energy of HOMO, LUMO and $T_1$ in eV) of the most preferred molecules (See pages 4 and 5 above.).

TABLE 1

| Compound | HOMO (eV) | LUMO (eV) | $T_1$ (eV) |
|---|---|---|---|
| 1(a) | −4.86 | −0.88 | 2.66 |
| 2(a) | −4.51 | −0.66 | 2.62 |

Many of the inventive compounds can be synthesized, in part, by using the following: standard Grignard chemistry, metal-mediated coupling of aryl halides with organo-boron reactants and amines, or a combination thereof. The inventive compounds can be used as charge transporting layers (e.g., HTL and/or ETL layers) and other layers in an OLED device, for example, as emission layers, charge blocking layers and charge generation layers.

I. Synthesis of Compound 1(a)

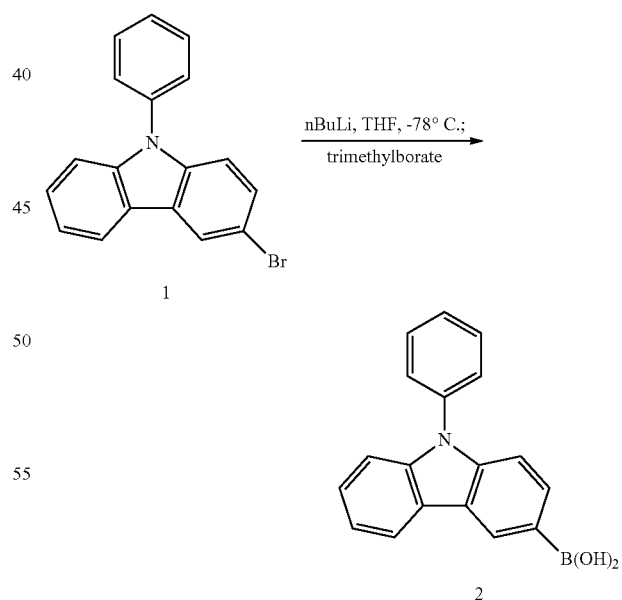

a) Synthesis of (9-phenyl-9H-carbazol-3-yl)boronic acid (2)

A 3 necked 250 mL round bottomed flask, equipped with a stir bar, thermocouple, and water condenser, and with a nitrogen inlet, was charged with 3-bromo-N-phenylcarbazole (1) (5.00 g, 15.52 mmol) and anhydrous tetrahydrofuran (THF) (65 mL) and was cooled to −73° C. internal temperature using a dry ice/isopropanol bath. N-Butyllithium (n-BuLi) (1.6 M in hexanes, 11.6 mL, 18.6 mmol) was added over 10 minutes, and the reaction was stirred at this temperature for 1 hour (h). Trimethylborate (2.4 mL, 23.1 mmol) was added, and the ice bath was removed. After 4 hours, the reaction was quenched with water, extracted with ethyl acetate, dried with magnesium sulfate, and concentrated by rotary evaporation to provide compound (2) as white solids (4.6 g). The material was taken into the next reaction without further purification. $^1$H NMR (400 MHz, Chloroform-d) δ 9.15 (t, J=0.9 Hz, 1H), 8.44-8.35 (m, 2H), 7.69-7.58 (m, 3H), 7.58-7.48 (m, 2H), 7.48-7.35 (m, 4H). $^{13}$C NMR (101 MHz, CDCl$_3$) δ 143.86, 141.24, 137.48, 133.36, 129.93, 128.71, 127.72, 127.21, 125.90, 123.65, 123.32, 120.61, 109.95, 109.37.

was dissolved in toluene (30 mL), and was precipitated with hexanes (90 mL) (solids started to form after 60 mL added). The precipitate was isolated by vacuum filtration to give pure product (4) (8.3 g, 20.8 mmol, 63%). $^1$H NMR (400 MHz, Chloroform-d) δ 8.30 (dd, J=1.8, 0.7 Hz, 1H), 8.18 (dt, J=7.8, 1.0 Hz, 1H), 7.65-7.54 (m, 9H), 7.51-7.39 (m, 4H), 7.31 (ddd, J=8.0, 5.2, 3.0 Hz, 1H). $^{13}$C NMR (101 MHz, CDCl$_3$) δ 141.42, 140.94, 140.54, 137.56, 132.16, 131.83, 129.95, 128.88, 127.62, 127.08, 126.28, 125.16, 123.95, 123.34, 120.71, 120.37, 120.17, 118.64, 110.15, 109.99.

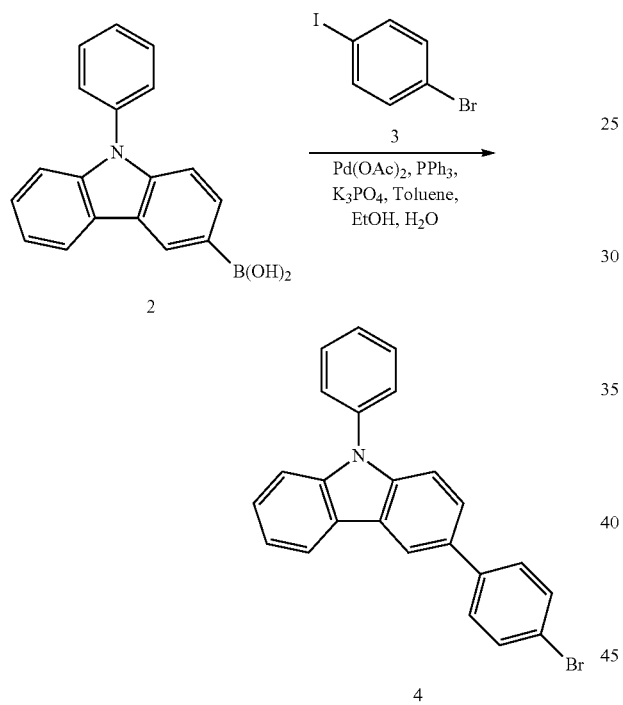

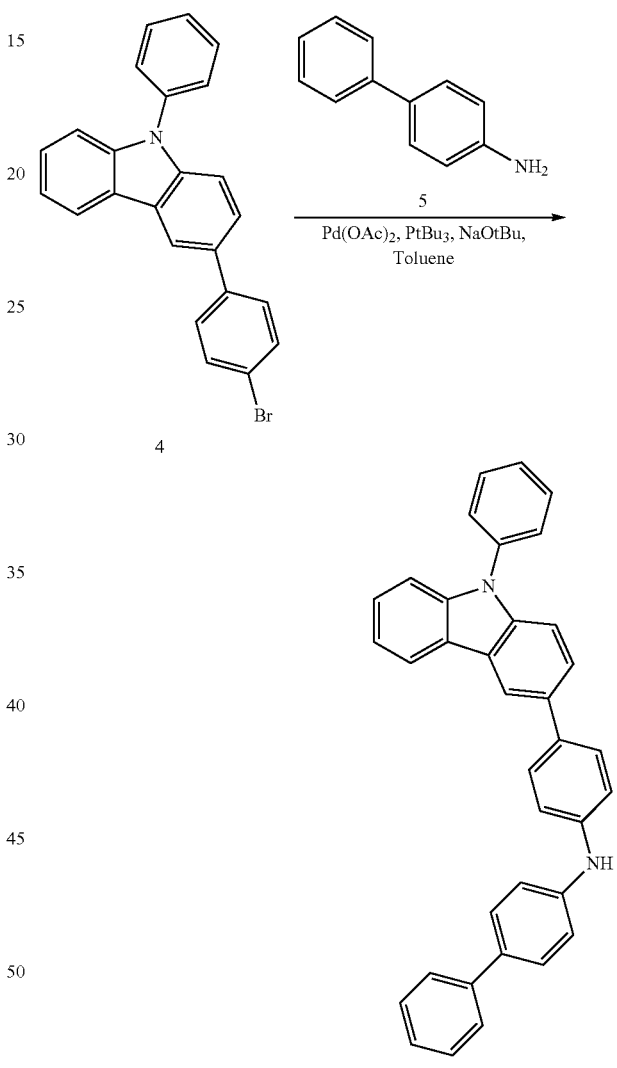

b) Synthesis of 3-(4-bromophenyl)-9-phenyl-9H-carbazole (4)

A 3 necked 500 mL round bottomed flask, equipped with a stir bar, a thermocouple, and a water condenser, and with nitrogen inlet, was charged with phenyl carbazole boronic acid (2) (9.5 g, 33.06 mmol), 1-iodo-4-bromobenzene (3) (9.37 g, 33.12 mmol), palladium acetate (0.139 g, 0.62 mmol), triphenyl phosphine (0.449 g, 1.71 mmol), and toluene 140 mL). Then 44 g of "40% (w/w) potassium phosphate tribasic diluted with water (46 mL) and ethanol (46 mL)" were added and the reaction heated to 75° C. (reflux). After 2 hours, the reaction was allowed to cool to room temperature, and the mixture was extracted with ethyl acetate. The combined organic layers were dried over magnesium sulfate, filtered, and concentrated. The crude material was purified on the combiflash (hexane/5% ethyl acetate) to give approximately 9 g of product. The material c) Synthesis of N-(4-(9-phenyl-9H-carbazol-3-yl)phenyl)-[1,1'-biphenyl]-4-amine (6)

A 250 mL three necked round bottomed flask, equipped with a stir bar, thermocouple, heating mantle, and water condenser, and with a nitrogen inlet, was charged with 3-(4-bromophenyl)-N-phenylcarbazole (4) (4.46 g, 11.2 mmol), 4-aminobiphenyl (5) (2.11 g, 12.5 mmol), sodium t-butoxide (2.18 g, 22.7 mmol) and palladium acetate (0.053 g, 0.24 mmol) and the flask was purged with nitrogen for 5 minutes. Toluene (67 mL) that had been degassed with nitrogen for 5 minutes was added followed by tri-tert-butylphosphine (0.120 g, 0.6 mmol) dissolved in toluene (3 mL) and the reaction heated to 110° C. (start time: 5 PM). After 16.5 h, HPLC showed very little conversion to product so more sodium t-butoxide (1.0 g) was added followed by Pd(dppf)Cl2 chloroform adduct (0.20 g). After 39 h, the reaction was cooled to room temperature and partitioned between water and ethyl acetate. The aqueous layer was extracted with ethyl acetate and the combined organic layers were dried over magnesium sulfate, filtered, and concentrated. The crude material was dissolved in methylene chloride and concentrated onto ~40 g of silica gel and purified on the combiflash (0 to 30% methylene chloride/hexanes). Fractions 36-60 were collected to provide amine compound (6) in 97% purity (3.22 g, 6.62 mmol, 59%). $^1$H NMR (400 MHz, Chloroform-d) δ 8.32 (dd, J=1.8, 0.7 Hz, 1H), 8.18 (dt, J=7.7, 1.0 Hz, 1H), 7.69-7.50 (m, 11H), 7.50-7.37 (m, 6H), 7.36-7.26 (m, 2H), 7.25-7.14 (m, 4H), 5.82 (s, 1H). $^{13}$C NMR (101 MHz, CDCl$_3$) δ 141.35, 137.74, 129.91, 128.75, 127.47, 127.09, 126.61, 126.09, 123.53, 120.36, 120.02, 109.92.

129.57, 128.93, 121.40, 119.74, 118.00, 109.49, 108.56, 77.34, 77.02, 76.70, 10.93, 8.85.

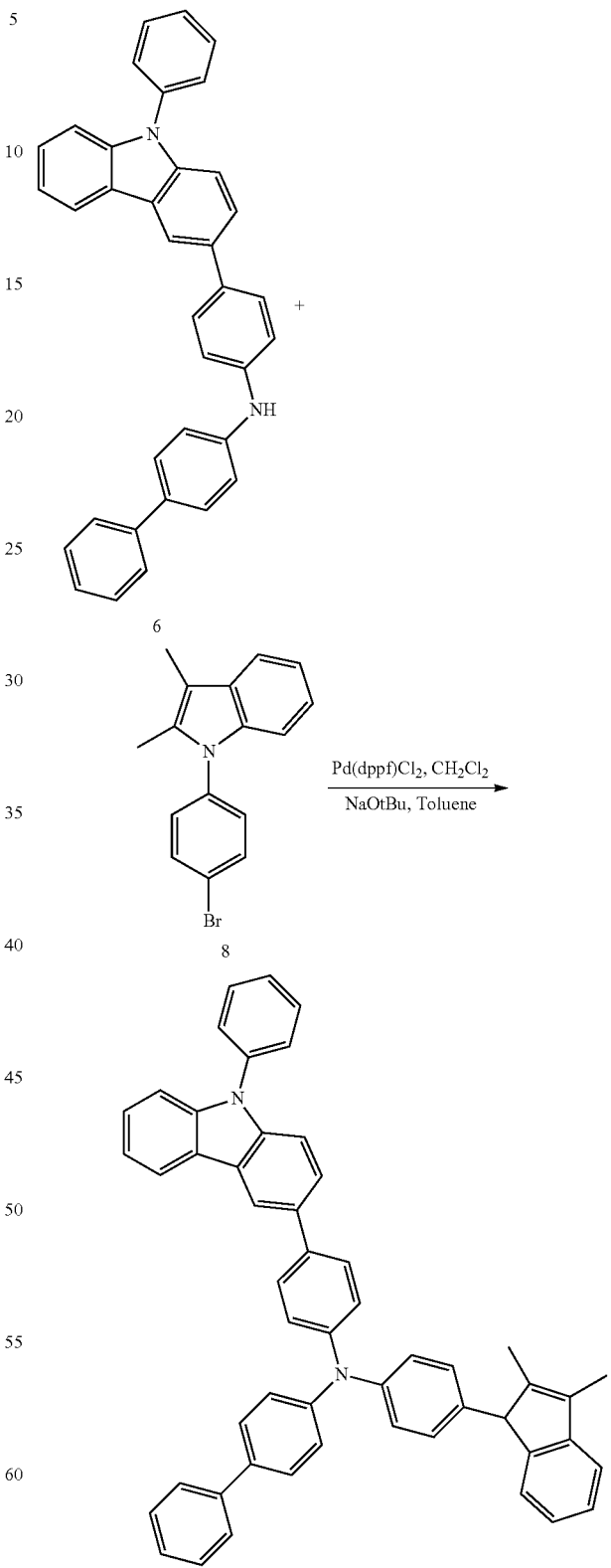

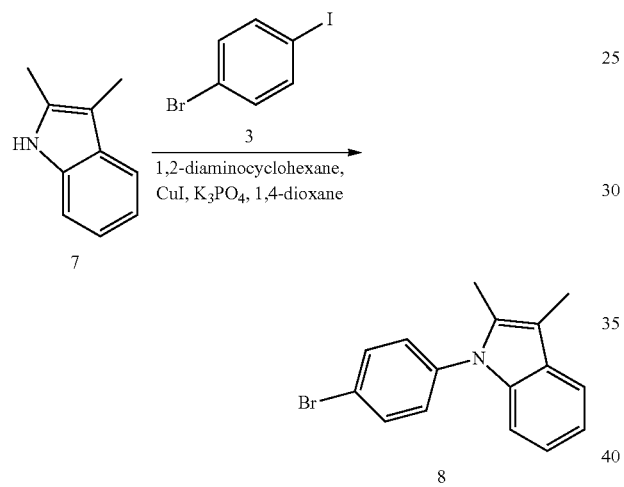

d) Synthesis of 1-(4-bromophenyl)-2,3-dimethyl-1H-indole (8)

A three necked 500 mL round bottomed flask, equipped with a stir bar, a thermocouple, and a water condenser, and with a nitrogen inlet, was charged with 2,3-dimethylindole (7) (5.00 g, 34.43 mmol), 1-bromo-4-iodobenzene (3) (9.74 g, 34.43 mmol), and 1,4-dioxane (350 mL). Copper iodide (0.330 g, 1.73 mmol), potassium phosphate tribasic (16.7 g, 78.67 mmol), and 1,2-diaminocyclohexane (0.45 mL, 3.94 mmol) were added and the reaction heated to 100° C. (start time 9:45 AM). After 24 h, the reaction had only gone to ~50% conversion so more copper iodide (0.320 g) was added. Potassium carbonate (5.2 g) and 1,2-diaminocyclohexane (0.45 mL) were also added. After 47 h, the reaction was cooled to room temperature and filtered through a plug of silica gel with ethyl acetate and concentrated. The crude material was dissolved in methylene chloride and concentrated onto silica gel (~40 g) and purified on the combiflash (0 to 5% ethyl acetate/hexanes). The product containing fractions were collected and concentrated to provide indole compound (8) as white solids (4.62 g, 15.4 mmol, 45%). $^1$H NMR (400 MHz, Chloroform-d) δ 7.64 (d, J=8.6 Hz, 2H), 7.57-7.48 (m, 1H), 7.21 (d, J=8.6 Hz, 2H), 7.17-7.02 (m, 3H), 2.30 (q, J=0.7 Hz, 3H), 2.22 (t, J=0.8 Hz, 3H). $^{13}$C NMR (101 MHz, CDCl$_3$) δ 137.43, 137.10, 132.60, 132.44, Compound 1(a)

e) Synthesis of N-(4-(2,3-dimethyl-1H-indol-1-yl)phenyl)-N-(4-(9-phenyl-9H-carbazol-3-yl)phenyl)-[1,1'-biphenyl]-4-amine N-(4-(2,3-dimethyl-1H-indol-1-yl)phenyl)-N-(4-(9-phenyl-9H-carbazol-3-yl)phenyl)-[1,1'-biphenyl]-4-amine (Compound 1(a))

A 100 mL three necked round bottomed flask, equipped with a stir bar, thermocouple, heating mantle, and water condenser, and with a nitrogen inlet, was charged with amine compound (6) (3.010 g, 6.2 mmol), N-(4-bromophenyl)-2,3-dimethylindole (8) (1.860 g, 6.2 mmol), sodium t-butoxide (0.884 g, 9.2 mmol), and Pd(dppf)Cl$_2$ CH$_2$Cl$_2$ adduct (0.101 g, 0.12 mmol) and the flask was purged with nitrogen. Toluene (62 mL) that had been degassed with nitrogen bubbling was added and the reaction heated to 100° C. After 24 h, the reaction was cooled to room temperature and partitioned between water and ethyl acetate. The aqueous layer was extracted with ethyl acetate and the combined organic layers were dried over magnesium sulfate, filtered and concentrated by rotary evaporator. The crude material was dissolved in methylene chloride and concentrated onto silica gel (~30 g) and purified on the combiflash (10 to 25% dichloromethane/hexanes). Fractions 8-25 were collected, concentrated, and dried in a vacuum oven (4 h, 50° C.) to provide the Compound 1(a) as a pale yellow solid (3.15 g, 4.46 mmol, 72%) with 99.49% purity. Sublimation provided material that was 99.68% pure. DSC Analysis—Tg—130° C. $^1$H NMR (400 MHz, Chloroform-d) δ 8.35 (d, J=1.7 Hz, 1H), 8.17 (dt, J=7.9, 1.0 Hz, 1H), 7.70-7.51 (m, 12H), 7.50-7.38 (m, 6H), 7.34-7.25 (m, 8H), 7.21-7.15 (m, 3H), 7.15-7.07 (m, 2H), 2.32 (d, J=0.8 Hz, 3H), 2.28 (d, J=0.9 Hz, 3H). $^{13}$C NMR (101 MHz, CDCl$_3$) δ 146.89, 146.84, 146.04, 141.40, 140.60, 140.29, 137.70, 137.46, 137.25, 135.92, 133.03, 132.87, 132.42, 129.94, 128.82, 128.79, 128.76, 128.27, 128.06, 127.54, 127.09, 126.99, 126.76, 126.18, 125.27, 125.21, 124.59, 123.96, 123.84, 123.51, 121.06, 120.37, 120.12, 119.40, 118.46, 117.86, 110.09, 109.97, 109.83, 107.73, 11.06, 8.93.

II. Synthesis of Compound 2(a)

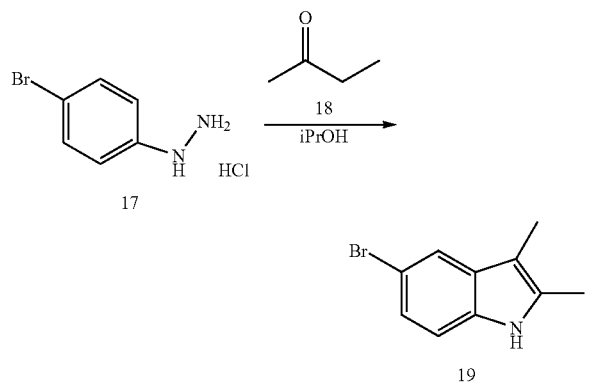

a) Synthesis of 5-bromo-2,3-dimethyl-1H-indole (19)

A 500 mL three neck round bottomed flask, equipped with a stir bar, thermocouple, heat mantle, and water condenser, and with a nitrogen inlet, was charged with 3-bromophenylhydrazine hydrochloride (17) (19.84 g, 88.77 mmol) and isopropanol (240 mL). 2-Butanone (18) (8.0 mL, 89.32 mmol) was added and the reaction was heated to 80° C. After 4 days, the reaction was allowed to cool to room temperature. The solvent was removed by rotary evaporation and the red residue dissolved in ethyl acetate (200 mL). The organic layer was washed with 1N HCl (100 mL) and saturated aqueous sodium bicarbonate (100 mL). The organic layer was dried over magnesium sulfate, filtered, and concentrated by rotary evaporation to give indole compound (19) as red solids (15.94 g, 71.1 mmol, 80%). $^1$H NMR (400 MHz, Chloroform-d) δ 7.70 (s, 1H), 7.59-7.55 (m, 1H), 7.17 (dd, J=8.5, 1.9 Hz, 1H), 7.11 (dd, J=8.4, 0.6 Hz, 1H), 2.35 (d, J=0.8 Hz, 3H), 2.17 (q, J=0.7 Hz, 3H). $^{13}$C NMR (101 MHz, CDCl$_3$) δ 133.77, 132.10, 131.27, 123.54, 120.61, 112.26, 111.35, 107.02, 11.58, 8.35.

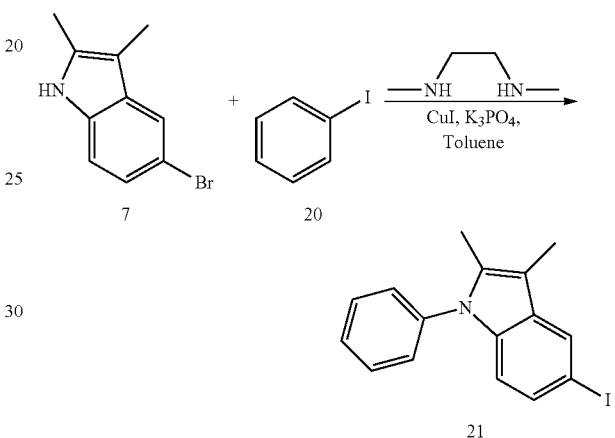

b) Synthesis of 5-iodo-2,3-dimethyl-1-phenyl-1H-indole (21)

In a nitrogen glove box, a 0.5 L round bottomed flask was filled with toluene (300 mL). The flask was then charged with indole compound (19) (15.g, 67.0 mmol), CuI (12.76 g, 67 mmol), K$_3$PO$_4$ (28.452 (134 mmol), and the diamine compound (N,N'-dimethyethylenediamine) (10.82 mL, 100 mmol). The mixture was stirred and iodobenzene (20) (15 mL, 134 mmol) was added. The flask was fitted with a Stevens condenser and was refluxed for 3 days. The reaction was monitored by GC-MS and it was shown that indole compound (19) was completely consumed. The reaction was allowed to cool to room temperature and was taken out of the box and poured into a 1 L round bottomed flask that contained Et$_2$O (500 mL). A precipitate formed and the mixture was filtered. Upon sitting for an additional 30 minutes more, a precipitate formed which was also filtered away. The crude product was isolated upon removing the organic solvent to provide indole compound (21) as a dark oil. The oil was deposited on silica using CH$_2$Cl$_2$ as the solvent. Purification by column chromatograph (0-15% CH$_2$Cl$_2$ in hexane) using a 340 g column afforded 12 g (51.5% yield) of indole compound (21) that contained ca.10% of the bromo-derivative of 21. $^1$H NMR (400 MHz, CDCl$_3$) δ 7.84 (d, J=1.7 Hz, 1H), 7.50 (m, 2H), 7.42 (m, 1H), 7.36-7.23 (m, 3H), 6.84 (d, J=8.5 Hz, 1H), 2.25 (s, 3H), 2.20 (s, 3H). $^{13}$C NMR (101 MHz, CDCl$_3$) δ 137.90, 136.58, 134.01, 131.49, 129.61, 129.41, 128.01, 127.88, 126.91, 111.86, 107.45, 82.96, 11.05, 8.90.

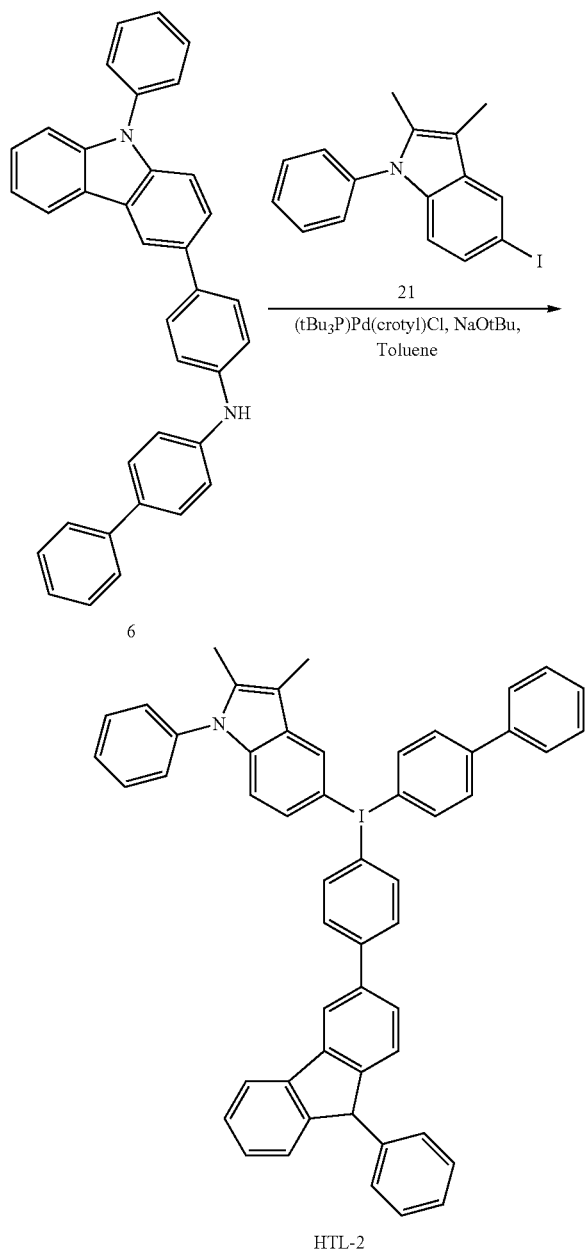

Compound 2(a)

c) Synthesis of N-([1,1'-biphenyl]-4-yl)-2,3-dimethyl-1-phenyl-N-(4-(9-phenyl-9H-carbazol-3-yl)phenyl)-1H-indol-5-amine (Compound 2(a))

In a nitrogen glove box, a 250 mL round bottomed flask was charged with amine compound (6) (4.00 g, 8.22 mmol), indole compound (21) (2.71 g, 7.82 mmol) NaOtBu (1.13 g, 11.74 g) and (tBu3P)Pd(crotyl)Cl (0.125 g). Toluene (150 mL) was added and the mixture was stirred at 110° C. overnight. Analysis the following day by GC-MS showed complete consumption of amine compound (6). The reaction was taken out of the glove box and treated with EtOAc (300 mL) and water (200 mL). The organic layer was isolated, dried with MgSO4, and filtered. The solvent was removed under reduced pressure to afford crude Compound 2(a).

Purification was undertaken by column chromatography (0-30% $CH_2Cl_2$ in hexane) using a 340 g column. High purity 99.8% product (4.1 g, 74.2% yield) was afforded as a colorless powder. DSC Analysis—Tg—133° C. $^1$H NMR (400 MHz, $C_6D_6$) δ 8.41 (d, J=1.7 Hz, 1H), 8.10 (dd, J=7.1, 1.5 Hz, 1H), 7.81 (d, J=2.0 Hz, 1H), 7.68-7.62 (m, 3H), 7.53 (d, J=2.8 Hz, 3H), 7.53-7.45 (m, 6H), 7.35-7.29 (m, 3H), 7.29-7.18 (m, 7H), 7.14 (d, J=2.3 Hz, 1H), 7.13-6.99 (m, 7H), 2.08 (s, 3H), 1.93 (s, 3H). $^{13}$C NMR (101 MHz, $C_6D6$) δ 148.96, 148.07, 141.88, 141.53, 140.80, 140.63, 138.76, 138.24, 136.07, 135.75, 134.44, 134.02, 133.72, 130.86, 129.98, 129.59, 129.05, 128.69, 128.52, 127.68, 127.50, 127.35, 127.03, 126.78, 126.39, 125.73, 124.62, 124.28, 124.00, 122.91, 122.14, 120.88, 120.48, 118.89, 117.22, 111.35, 110.40, 110.23, 108.84, 10.86, 8.97.

OLED Device Fabrication and Testing

All organic materials were purified by sublimation before deposition. OLEDs were fabricated onto an indium tin oxide (ITO) coated glass substrate that served as the anode, and topped with an aluminum cathode. All organic layers were thermally deposited by chemical vapor deposition, in a vacuum chamber with a base pressure of <$10^{-7}$ torr. The deposition rates of organic layers were maintained at 0.1~0.05 nm/s. The aluminum cathode was deposited at 0.5 nm/s. The active area of the OLED device was "3 mm×3 mm," as defined by the shadow mask for cathode deposition.

Each cell, containing HIL, HTL, EML host, EML dopant, ETL, or EIL materials, was placed inside a vacuum chamber, until it reached $10^{-6}$ torr. To evaporate each material, a controlled current was applied to the cell containing the material, to raise the temperature of the cell. An adequate temperature was applied to keep the evaporation rate of the materials constant throughout the evaporation process.

For the HIL layer, N1,N1'-([1,1'-biphenyl]-4,4'-diyl)bis (N1-(naphthalen-1-yl)-N4,N4-diphenylbenzene-1,4-diamine) was evaporated at a constant 1 Angstrom/second (A/s) rate, until the thickness of the layer reached 600 Angstrom. Simultaneously, the HTL compounds were evaporated at a constant 1 A/s rate, until the thickness reached 200 Angstrom. The N4,N4'-di(naphthalen-1-yl)-N4, N4'-diphenyl-[1,1'-biphenyl]-4,4'-diamine (NPB) was used as a reference material for the HTL material to compare with the inventive compounds 1(a) and 2(a).

For the EML layer, 9,10-di(naphthalen-2-yl)anthracene (ADN, host material) and (E)-4,4'-(ethene-1,2-diyl)bis-(N,N-diphenylaniline)(DPAVB, dopant) were co-evaporated, until the thickness reached 350 Angstrom. The deposition rate for the host material was 0.98 A/s, and the deposition for the dopant material was 0.02 A/s, resulting in a 2% doping of the host material. For the ETL layer, tris(8-hydroxyquinolinato)aluminum (Alq3) was evaporated at a constant 1 A/s rate, until the thickness reached 300 Angstrom. Finally, "20 Angstrom" of a thin electron injection layer (EIL) (Liq) was evaporated at a 0.2 A/s rate. See Table 2 below.

TABLE 2

| Device Materials | | |
| --- | --- | --- |
| | Name | Commercial Name |
| Hole Injection Layer (HIL) Material | N1,N1'-([1,1'-biphenyl]-4,4'-diyl)bis(N1-(naphthalen-1-yl)-N4,N4-diphenylbenzene-1,4-diamine) | — |
| Hole Transporting Layer (HTL) Material | N4,N4'-di(naphthalen-1-yl)-N4,N4'-diphenyl-[1,1'-biphenyl]-4,4'-diamine | NPB |

TABLE 2-continued

Device Materials

| | Name | Commercial Name |
|---|---|---|
| Fl Blue Host Material (EML Layer) | 9,10-di(naphthalen-2-yl)anthracene | ADN |
| Fl Blue Dopant (EML Layer) | (E)-4,4'-(ethane-1,2-diyl)bis(N,N-diphenylaniline) | DPAVB |
| Reference Electron Transport Layer (ETL) Material | tris(8-hydroxyquinolinato)aluminum | Alq3 |
| Electron Injection Layer (EIL) Material | lithium quinolate | Liq |

The current-voltage-brightness (J-V-L) characterizations for the OLED devices were performed with a source measurement unit (KEITHLY 238) and a luminescence meter (MINOLTA CS-100A). EL spectra of the OLED devices were collected by a calibrated CCD spectrograph.

Inventive Compounds

Inventive Compounds 1(a) and 2(a) were each further purified by sublimation, and incorporated into OLED devices for preliminary evaluation against the reference compound (NPB). OLED devices were fabricated, as discussed above, on coated glass substrates with multiple organic layers sandwiched between a transparent ITO anode and an aluminum cathode.

Table 3 (below) shows the OLED device testing results of inventive Compound 2(a) mixed with Liq (50:50) compared to the reference compound (NPB). As seen in Table 3, the devices containing the inventive compound had better (higher) efficiency and better (lower) operating voltage over the device containing the reference compound.

TABLE 3

Device Data Luminous Efficiency

| HTL Compound | Voltage @1000 nit[1] [V] | Luminous Efficiency @1000 nit [Cd/A][2] | CIE[3] (X, Y) |
|---|---|---|---|
| NPB (Comparative) | 6.6 | 4.0 | 148, 150 |
| Compound 2(a) | 6.4 | 4.2 | 154, 178 |

[1]Nit = candela per square meter (Cd/m$^2$)
[2]Cd/A = candelas per ampere (Amp.)
[3]CIE = The International Commission on Illumination Stability Study using Cyclic Voltammetry Measurement Synthesis of Model Compound (9-(4-(2,3-dimethyl-1H-indol-1-yl)phenyl)-9H-carbazole) for This Study

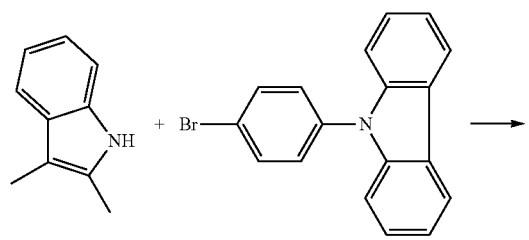

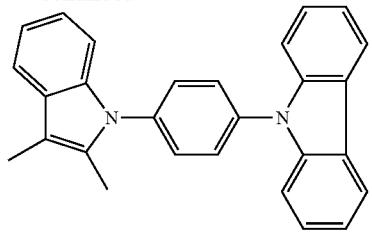

A suspension of powdered t-BuOK (192 mg, 2 mmol, 96), 10 mL of dry Toluene, and 2,3-dimethyl-1H-indole (145 mg, 1.2 mmol), 9-(4-bromophenyl)-9H-carbazole (322 mg, 1 mmol), Pd(OAc)$_2$ (2.16 mg, 1% mol, 0.01 mmol), X-Phos (4.77 mg, 1% mol, 0.01 mmol) were stirred vigorously at 90° C. for 24 hours under nitrogen. After cooling, water was added. The organic layer was extracted with brine, and the organic layer was dried with MgSO$_4$, filtered, and concentrated on a rotary evaporator, to obtain the crude product, which was then purified through column chromatography. Yield: 76% (9-(4-(2,3-dimethyl-1H-indol-1-yl)phenyl)-9H-carbazole).

Cyclic Voltammetry Measurement:

Cyclic voltammetry was performed on a CHI 760D electrochemical work station at room temperature, with a conventional three-electrode configuration consisting of an Pt plate (diameter: 2 mm) working electrode, a Pt wire counter electrode, and a Hg/Hg2+ reference electrode. DMF was used as solvent, and the supporting electrolyte was 0.1 M tetrabutylammonium hexafluorophosphate. The model compound was dissolved in the DMF (plus electrolyte) at 4 mmole per liter. The results are shown in FIG. 1. As seen in FIG. 1, the "Z moiety," as shown below, provides stability as seen by the good electrochemical reversibility in this FIGURE:

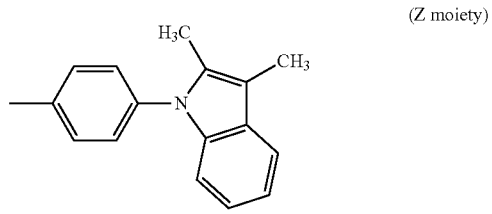

(Z moiety)

It is believed that other alkyl groups, in addition methyl, will also show good electrochemical reversibility. Such groups include, but are not limited to, linear or branched C1-C6 alkyls, and preferably include ethyl, propyl, n-butyl, i-butyl, and t-butyl.

The invention claimed is:
1. A composition comprising a compound of Structure 1:

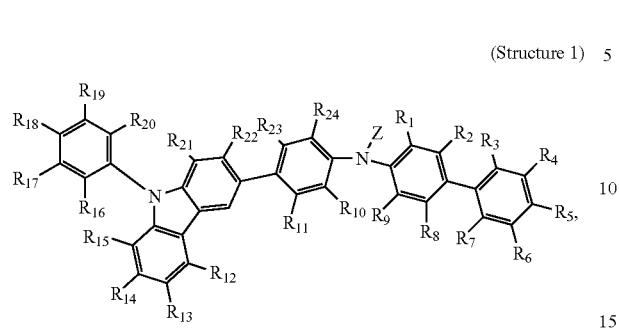

(Structure 1)

wherein $R_1$ through $R_{24}$ are each, independently, selected from the following: a hydrogen, a hydrocarbyl, a substituted hydrocarbyl, a cyano, an alkoxy, an aryloxy, or a $NR'_2$ wherein R' is selected from an aryl or a heteroaryl; and
wherein, optionally, two or more of $R_1$ to $R_{24}$ form one or more ring structures; and
wherein Z is selected from group (1) or (2):

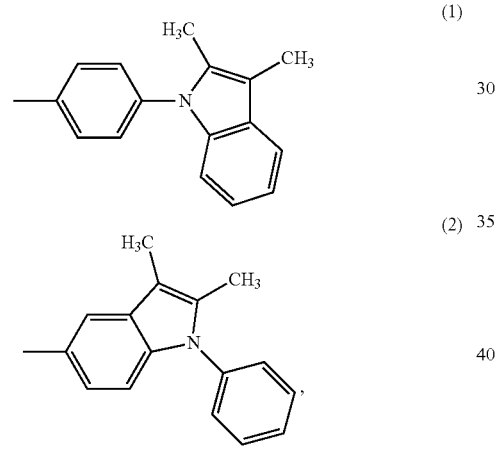

(1)

(2)

and
wherein, optionally, one or more hydrogens may be substituted with deuterium.

2. The composition of claim 1, wherein $R_1$ through $R_{24}$ are each independently selected from the following: hydrogen, an unsubstituted hydrocarbyl, or an substituted hydrocarbyl.

3. The composition of claim 1, wherein $R_1$ through $R_{24}$ are each hydrogen.

4. The composition of claim 1, wherein the Z is group (1):

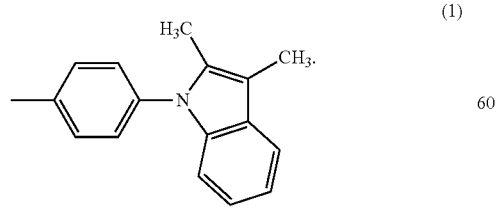

(1)

5. The composition of claim 1, wherein Structure 1 is the following Structure 1a:

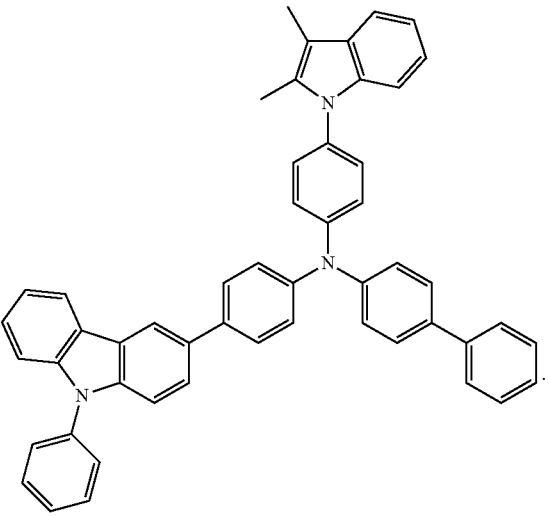

(Structure 1a)

6. The composition of claim 1, wherein Z is group (2):

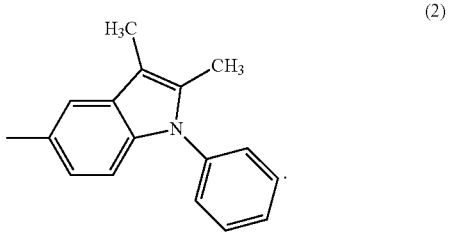 [SMILES: Cc1ccc2c(c1)c(C)c(C)n2-c1ccccc1]

(2)

7. The composition of claim 6, wherein Structure 1 is Structure 2a:

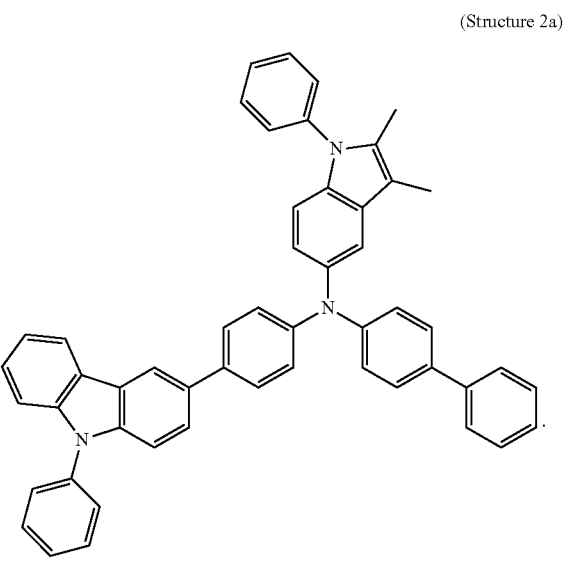 [SMILES: Cc1c(C)n(-c2ccccc2)c2ccc(N(c3ccc(-c4ccccc4)cc3)c3ccc(-c4ccc5c(c4)c4ccccc4n5-c4ccccc4)cc3)cc12]

(Structure 2a)

8. The composition of claim 1, wherein the compound of Structure 1has a HOMO level of −5.00 eV to −4.40 eV.

9. The composition of claim 1, wherein the Z group of group 1, when attached to a carbazole via the nitrogen atom of the carbazole, provides an electrochemical stability within ±3.0 ×10-5 A, for at least 2 repeated cyclic voltammograms, each with a voltage range from 1.6 V to 0 V.

10. A film formed from the composition of claim 1.

11. An electronic device comprising at least one component formed from the film of claim 10.

12. An electronic device comprising at least one component formed from the composition of claim 1.

13. The electronic device of claim 12, wherein the component is a hole transport layer.

14. The electronic device of claim 13, further comprising a hole injection layer, an emitting layer, an electron charge transport layer, and/or an electron injection layer.

15. A composition comprising a compound of Structure 2:

(Structure 2)

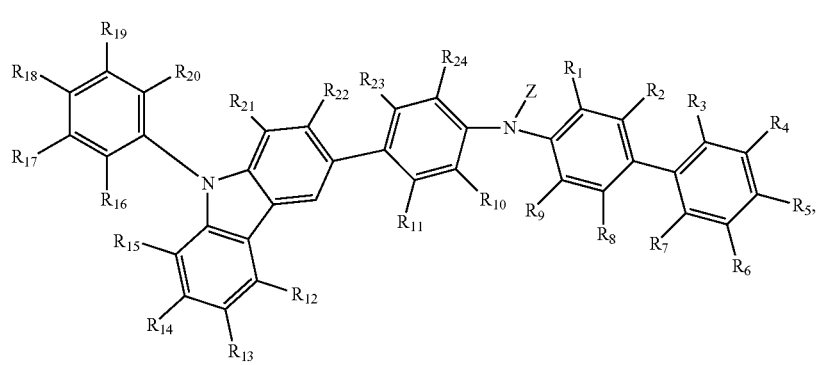

wherein $R_1$ through $R_{24}$ are each, independently, selected from the following: a hydrogen, a hydrocarbyl, a substituted hydrocarbyl, a cyano, an alkoxy, an aryloxy, or a $NR'_2$ wherein R' is selected from an aryl or a heteroaryl; and wherein, optionally, two or more of $R_1$ to $R_{24}$ form one or more ring structures; and wherein Z is selected from group (1a) or (2a):

(1a)

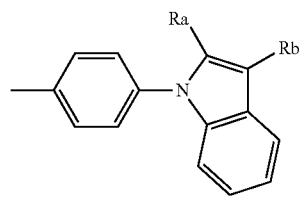

-continued (2a)

wherein for group 1a, Ra and Rb are each independently an alkyl, and wherein at least one of Ra and/or Rb comprises at least two carbon atoms; and for group 2a, Rc and Rd are each independently an alkyl, and wherein at least one of Rc and/or Rd comprises at least two carbon atoms; and wherein, optionally, one or more hydrogens may be substituted with deuterium.

* * * * *